United States Patent
Omura et al.

(10) Patent No.: US 9,295,438 B2
(45) Date of Patent: Mar. 29, 2016

(54) MOVABLE X-RAY GENERATION APPARATUS

(71) Applicant: CANON KABUSHIKI KAISHA, Tokyo (JP)

(72) Inventors: Satoru Omura, Chigasaki (JP); Tetsuo Shimada, Hachioji (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/172,191

(22) Filed: Feb. 4, 2014

(65) Prior Publication Data

US 2014/0233703 A1 Aug. 21, 2014

(30) Foreign Application Priority Data

Feb. 15, 2013 (JP) .................... 2013-028345

(51) Int. Cl.
*A61B 6/00* (2006.01)

(52) U.S. Cl.
CPC .............. *A61B 6/4405* (2013.01); *A61B 6/4452* (2013.01); *A61B 6/462* (2013.01); *A61B 6/463* (2013.01)

(58) Field of Classification Search
CPC .... A61B 6/4405; A61B 6/4452; A61B 6/462; A61B 6/463
USPC ................................ 378/198, 98.2
See application file for complete search history.

(56) References Cited

U.S. PATENT DOCUMENTS

| 5,586,162 A | 12/1996 | Grichnik ................ 378/198 |
| 5,712,482 A | 1/1998 | Gaiser et al. ............ 250/363.08 |

(Continued)

FOREIGN PATENT DOCUMENTS

| CN | 102247152 | 11/2011 |
| JP | 2006-081690 | 3/2006 |
| WO | 00/24234 A | 4/2000 |
| WO | 2012/056676 A | 5/2012 |

OTHER PUBLICATIONS

OrthoScan, "orthoscan support—Google Search", images published on or prior to Mar. 30, 2012, Retrieved from the Internet: <https://www.google.com/search?q=orthoscan&rls=com.microsoft%3Aen-US%3AIE-Address&biw=1133&bih=567&source=lnt&tbs=cdr%3A1%2Ccd_min%3A2000%2Ccd_max%3A3%2F30%2F2012&tbm=isch#tbs=cdr:1%2Ccd_min:2000%2Ccd_max:3%2F30%2F2012&t . . . >.*

(Continued)

*Primary Examiner* — Glen Kao
*Assistant Examiner* — Chih-Cheng Kao
(74) *Attorney, Agent, or Firm* — Fitzpatrick, Cella, Harper & Scinto

(57) ABSTRACT

A movable X-ray generation apparatus includes an X-ray tube configured to perform irradiation with X-rays, an arm configured to support the X-ray tube, a cart unit configured to support and move the arm, and a monitor mounted on the upper portion of the cart unit. The movable X-ray generation apparatus includes a first member configured to support the monitor to be pivotable about a first rotation axis, and a second member configured to support the first member to be pivotable about a second rotation axis different from the first rotation axis with respect to the cart unit. At least one of the first rotation axis and the second rotation axis provides a rotation axis parallel to the display surface of the monitor and perpendicular to a moving surface on which the cart unit moves.

11 Claims, 12 Drawing Sheets

(56) References Cited

U.S. PATENT DOCUMENTS

| | | | | |
|---|---|---|---|---|
| 6,256,374 | B1* | 7/2001 | Tomasetti et al. | 378/98.2 |
| 2004/0155167 | A1* | 8/2004 | Carter | 248/324 |
| 2008/0302926 | A1 | 12/2008 | Cheng et al. | 248/161 |
| 2010/0239073 | A1* | 9/2010 | Eaves | 378/198 |
| 2011/0049378 | A1 | 3/2011 | Omura | 250/370.15 |
| 2012/0195404 | A1 | 8/2012 | Omura | 378/62 |
| 2014/0098942 | A1 | 4/2014 | Omura et al. | 378/197 |

OTHER PUBLICATIONS

OrthoScan, "orthoscan-fd.mp4", Jan. 11, 2012, Retrived from the Internet: <https://www.youtube.com/watch?v=aq3wO_xd28Q>.*

British Search Report issued on Jul. 29, 2014 in British (GB) counterpart application 1402439.2.

Office Action issued on Sep. 8, 2015 in Chinese (P.R. China) counterpart application 201410046839.9, with translation.

* cited by examiner

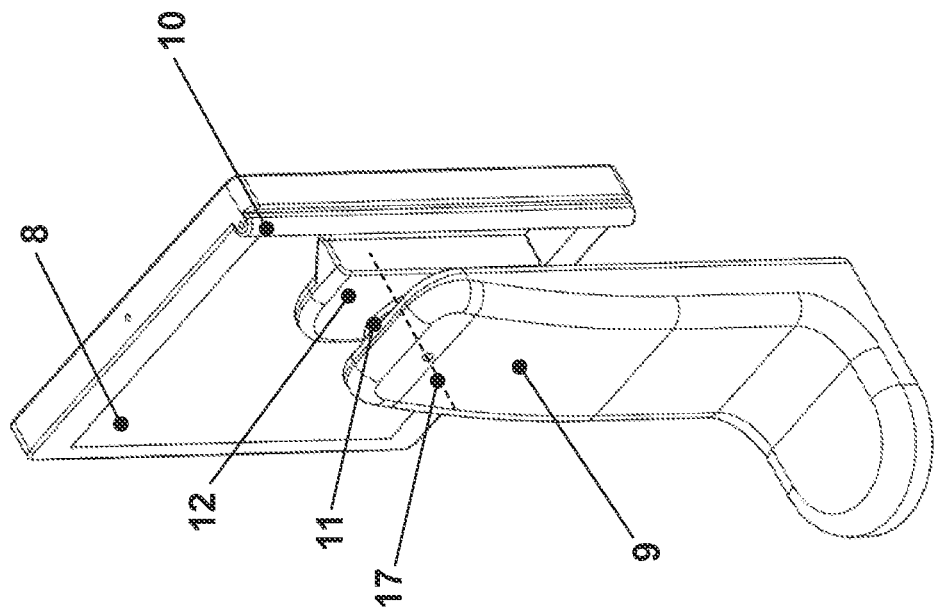
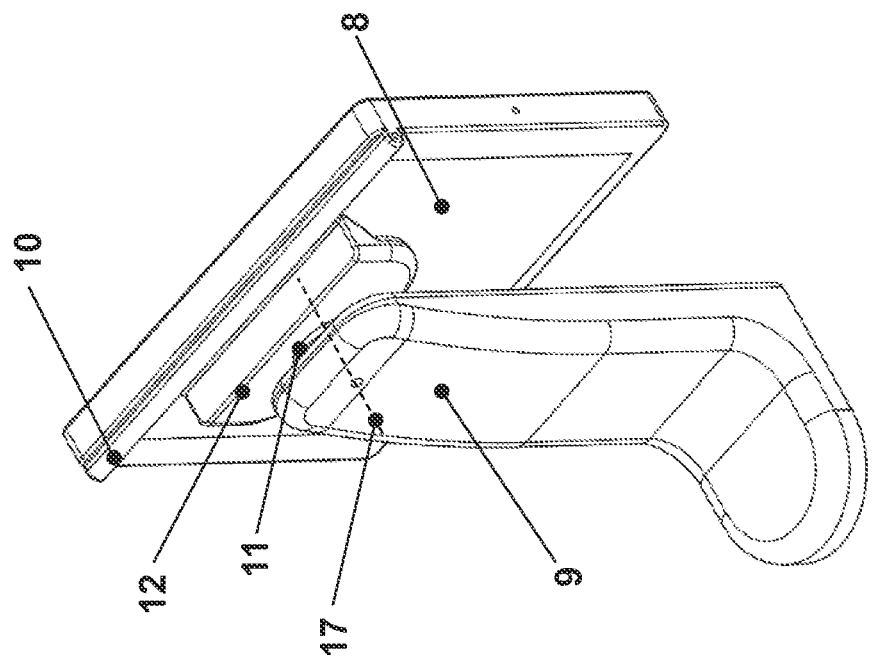

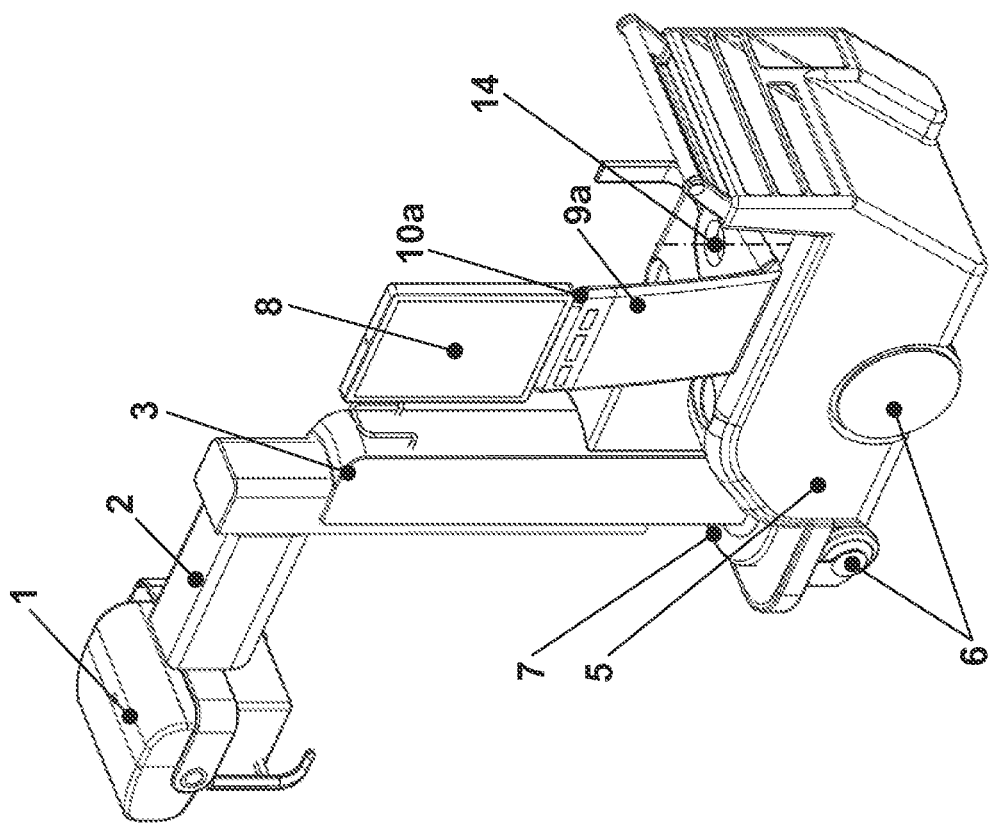
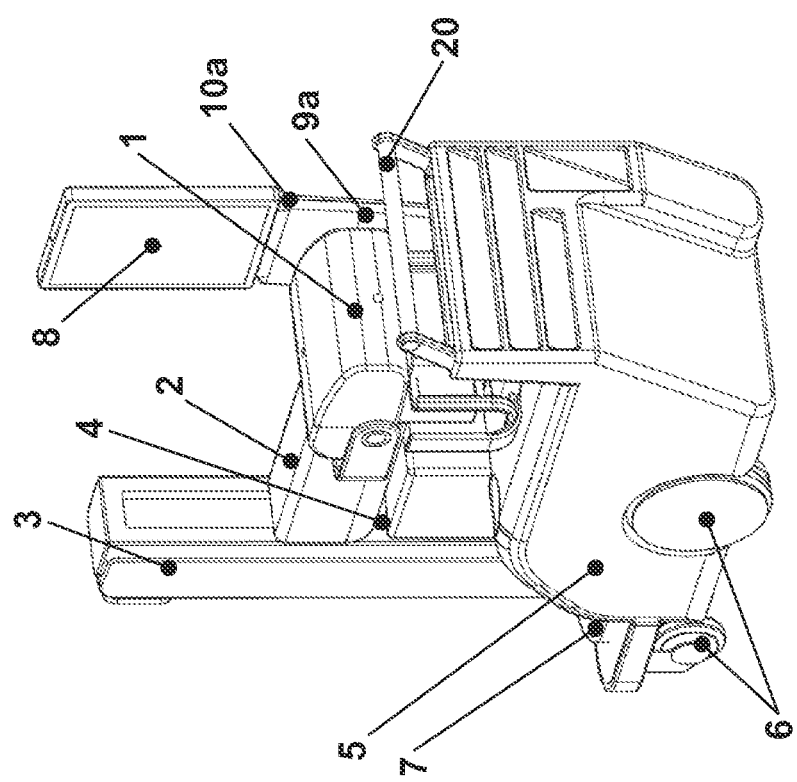

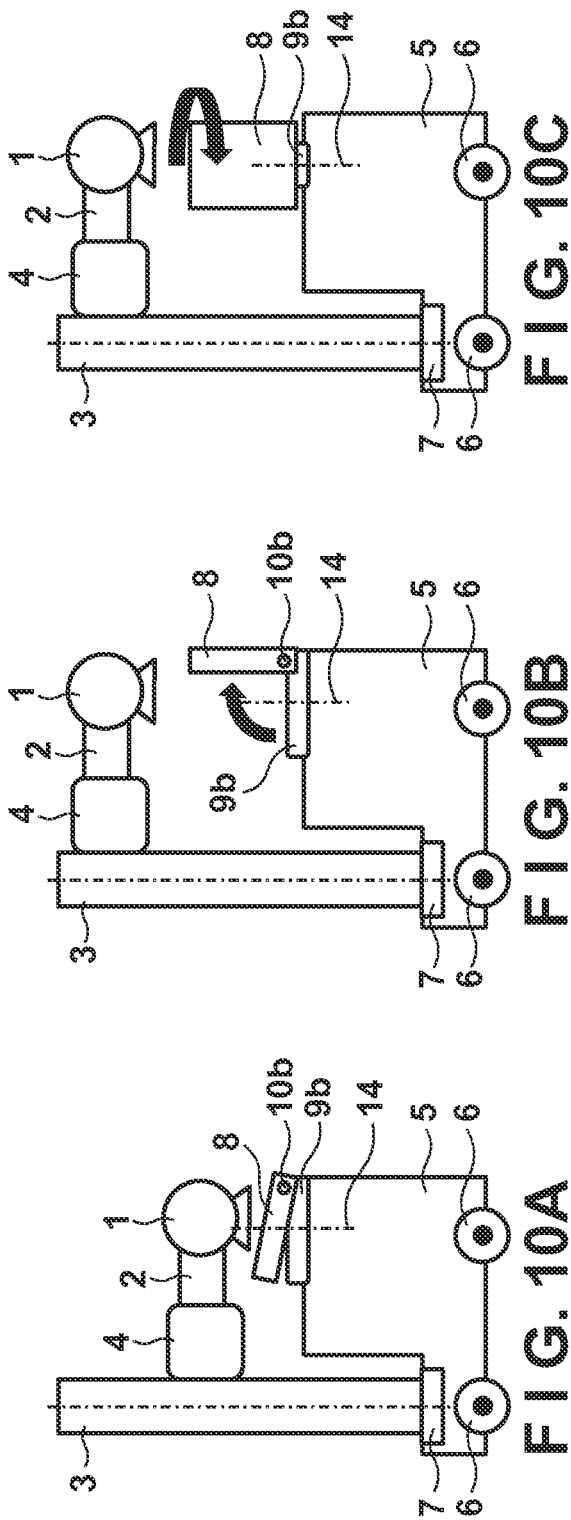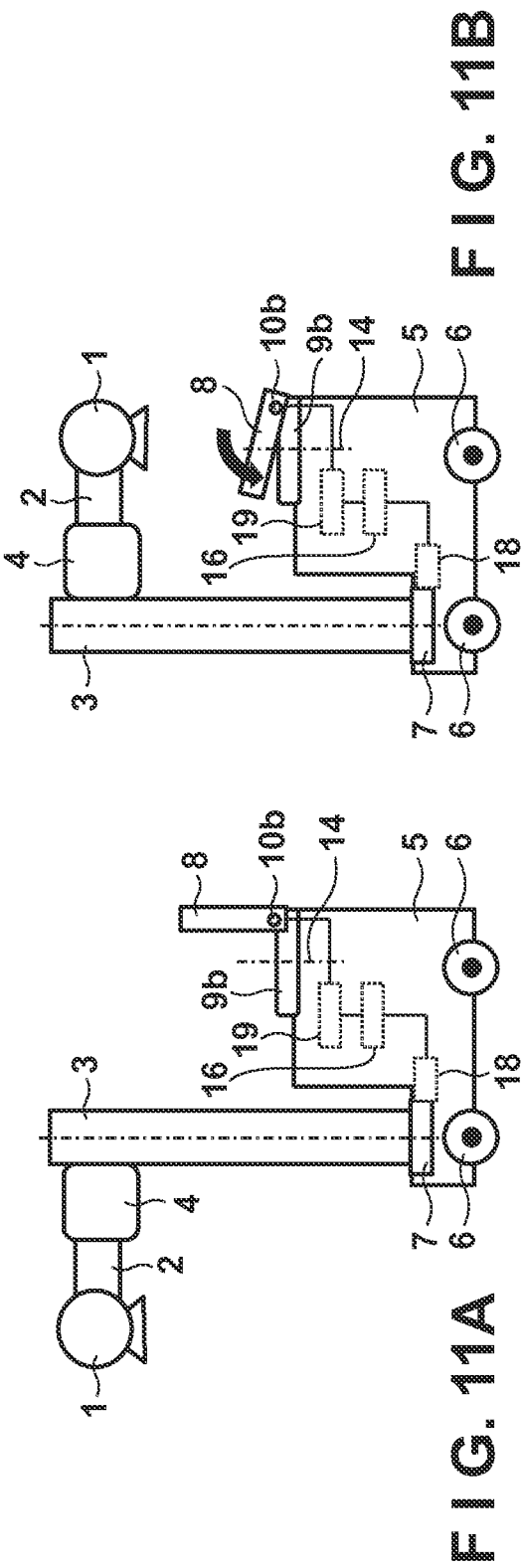

MOVABLE X-RAY GENERATION APPARATUS

BACKGROUND OF THE INVENTION

1. Field of the Invention

The present invention relates to a movable X-ray generation apparatus in which a radiation source for generating radiation to obtain a radiation image from radiation transmitted through an object is mounted on a cart.

2. Description of the Related Art

In recent years, as medical X-ray imaging apparatuses, there have been widely used a movable X-ray imaging machine which performs X-ray imaging in a hospital room or operating room and an X-ray imaging apparatus which holds, by a C-arm, an X-ray tube for performing irradiation with X-rays and an X-ray detector for detecting X-rays transmitted through a patient.

When performing X-ray imaging by using a movable X-ray imaging machine, the X-ray tube needs to include a mechanism for changing an X-ray irradiation position with respect to an object lying on a bed to place the X-ray tube above the object. When imaging one of the four limbs of the object, in particular, it is impossible to position the X-ray detector and X-ray tube to a preferable state and to capture a proper image unless it is possible to place the X-ray tube at any position on the bed. The movable X-ray imaging machine, therefore, adopts an arrangement which supports the X-ray tube by an arm movable with respect to the cart.

The movable X-ray imaging machine runs through the narrow space between beds in a hospital room and on corridors between hospital wards along which stretchers and other medical apparatuses come and go, and hence needs to be folded into a compact structure at the time of movement. For this purpose, the arm which supports the X-ray tube needs to have a structure such that the arm can be widely stretched out at the time of X-ray imaging and accommodated in small size at the time of movement. In Japanese Patent Laid-Open No. 2006-81690 an arm which supports an X-ray tube is configured to be extensible, thereby extending the arm at the time of X-ray imaging and contracting the arm to be accommodated at the time of movement.

When using the movable X-ray imaging machine in an operating room, a doctor may carry out an operation on a patient while checking an X-ray image captured by the movable X-ray imaging machine on a monitor. However, in the movable X-ray imaging machine described in Japanese Patent Laid-Open No. 2006-81690, since the position of the monitor is fixed on the machine, it may be impossible to check the monitor on the cart during X-ray imaging. For this reason, it is necessary to prepare an additional monitor. However, there are a number of medical apparatuses around an operating table and it is necessary to provide space for the additional monitor. That is, the arrangement position of the monitor may be limited by the operating procedure of an operation and the arrangement of apparatuses necessary for an emergency, thereby disabling an efficient operation.

SUMMARY OF THE INVENTION

An embodiment of the present invention provides a movable X-ray generation apparatus which includes an X-ray tube and a monitor including a screen and allows a doctor or operator to readily see the monitor screen while performing x-ray imaging.

According to one aspect of the present invention, there is provided a movable X-ray generation apparatus comprising: an X-ray tube configured to perform irradiation with X-rays; an arm configured to support the X-ray tube; a cart unit configured to support and move the arm; a monitor, including a screen, mounted on an upper portion of the cart unit, a first member configured to support the monitor to be pivotable about a first rotation axis; and a second member configured to support the first member to be pivotable about a second rotation axis different from the first rotation axis, wherein at least one of the first rotation axis and the second rotation axis is perpendicular to a plane contacted by the parts of the moving mechanism.

Further features of the present invention will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

BRIEF DESCRIPTION OF THE DRAWINGS

FIGS. 3A and 3B are views for explaining the swivel rotation of the monitor according to the first embodiment;

FIGS. 9A and 9B are views for explaining the movement of a monitor according to the second embodiment;

FIGS. 10A to 10C are schematic views each showing the outer appearance of a movable X-ray imaging apparatus according to the third embodiment;

FIGS. 11A and 11B are views for explaining a monitor accommodation system according to the third embodiment;

DESCRIPTION OF THE EMBODIMENTS

[First Embodiment]

Figure 1A:
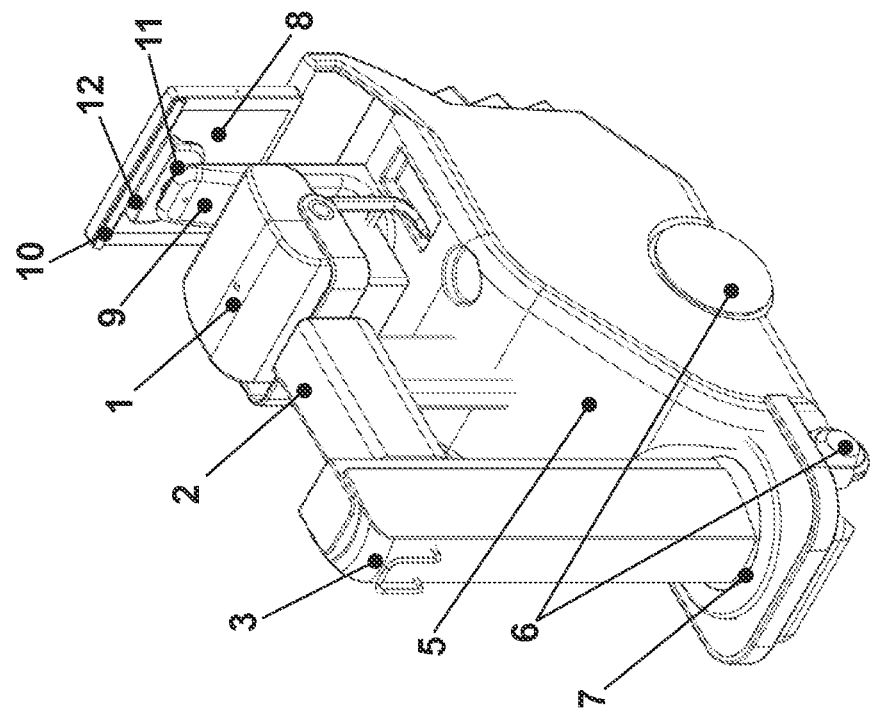
FIGS. 1A and 1B are views each showing the outer appearance of a movable X-ray imaging apparatus according to the first embodiment.
Figure 1B:
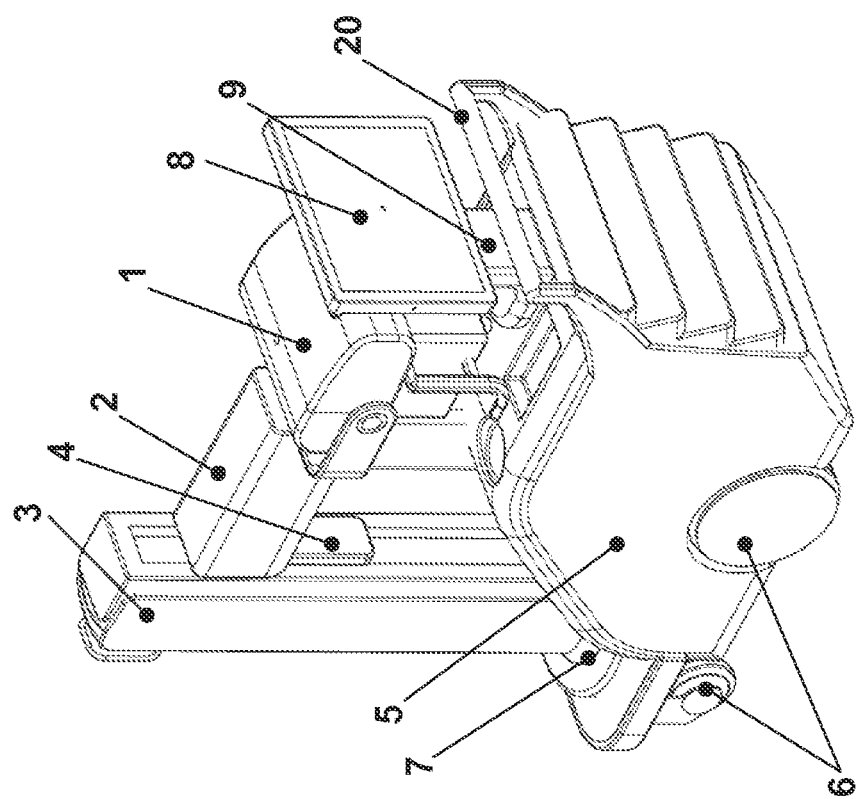

FIGS. 1A and 1B are views each showing the outer appearance of a movable X-ray generation apparatus according to the first embodiment. Note that the movable X-ray generation apparatus includes an X-ray tube serving as an X-ray source, and generally constitutes a movable X-ray imaging apparatus together with an X-ray detection cassette. The movable X-ray generation apparatus will be referred to as a movable X-ray imaging apparatus hereinafter. FIG. 1A is a perspective view showing the form of the apparatus at the time of movement (to be referred to as a moving form hereinafter) when seen from the back side. FIG. 1B is a perspective view showing the moving form of the apparatus when seen from the front side. Note that the front side and the back side indicate the leading side and the trailing side in the traveling direction when the user pushes the apparatus using a handle 20, respectively.

Referring to FIGS. 1A and 1B, an X-ray tube 1 serves as an X-ray source for generating X-rays, and irradiates an object with X-rays. An arm 2 supports the X-ray tube 1 and includes an extensible mechanism for moving the X-ray tube 1 in at least the horizontal direction and an extension/contraction position fixing mechanism. A column 3 supports the arm 2 with respect to a cart unit 5. An arm support unit 4 connects the arm 2 to the column 3, and includes a function of moving the arm 2 along the column 3 and fixing the arm 2 to the column 3 at an arbitrary position upon movement. The cart unit 5 supports the column 3. A moving mechanism 6 includes a plurality of tires or casters to move the cart unit 5 on the floor. A surface on which the cart unit 5 is moved by the moving mechanism 6 will be referred to as a moving surface hereinafter. The point at which each of the wheels or casters engage the moving surface is each a part of the moving mechanism. As such a plane contacted by each of these parts of the moving mechanism would contact the moving surface when in use. Throughout the description a reference to "the moving surface" should be construed as a reference to "the plane contacted by the parts of the moving mechanism". A column rotating unit 7 connects the cart unit 5 to the column 3 and includes a bearing mechanism for allowing the column 3 to rotate, on the cart unit 5, about an axis perpendicular to the moving surface by the moving mechanism 6. The column rotating unit 7 also includes a non-excitation brake, and can rotate the column 3 at an arbitrary position in the energization state of the non-excitation brake and stop the column 3 at an arbitrary position in the non-energization state of the non-excitation brake.

A monitor 8 is supported by a monitor support arm 9 arranged on the upper portion of the cart unit 5. A tilt hinge 10 and a swivel hinge 11 are connected via a monitor support member 12. The tilt hinge 10 is attached to the monitor 8. The swivel hinge 11 is attached to the monitor support arm 9. That is, the monitor 8 is supported by the monitor support arm 9 via the tilt hinge 10 and the swivel hinge 11. The tilt hinge 10 and the swivel hinge 11 are desirably torque hinges which can flexibly hold the attitude of the monitor but may be torque hinges each having low torque and including a mechanism which can lock at an arbitrary hinge opening angle, damper hinges, or a combination thereof. A mechanism which can lock the position of the monitor 8 with a desirable attitude of the monitor 8 may be provided.

Figure 2C:
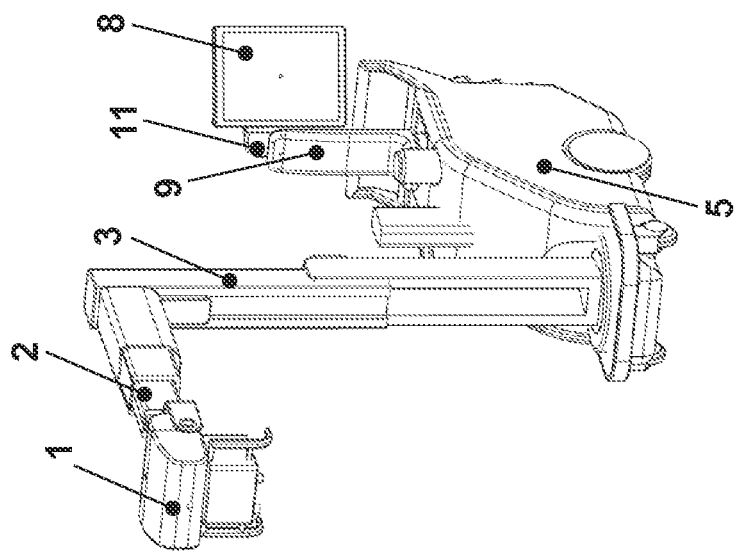
FIGS. 2A to 2C are views for explaining the movement of a monitor according to the first embodiment.
Figure 2B:
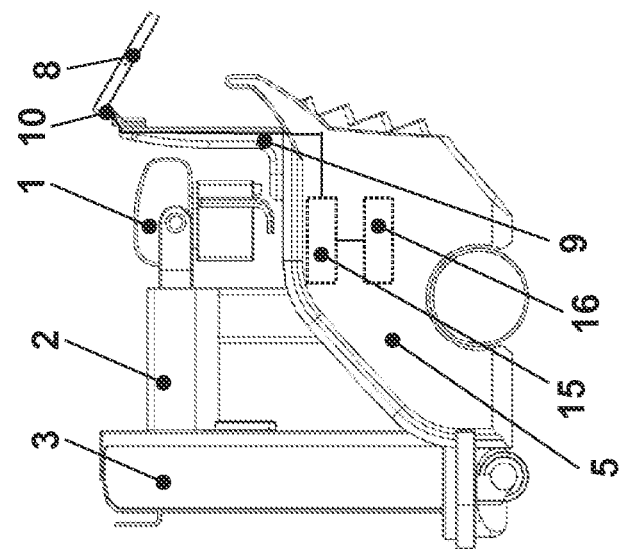
Figure 2A:
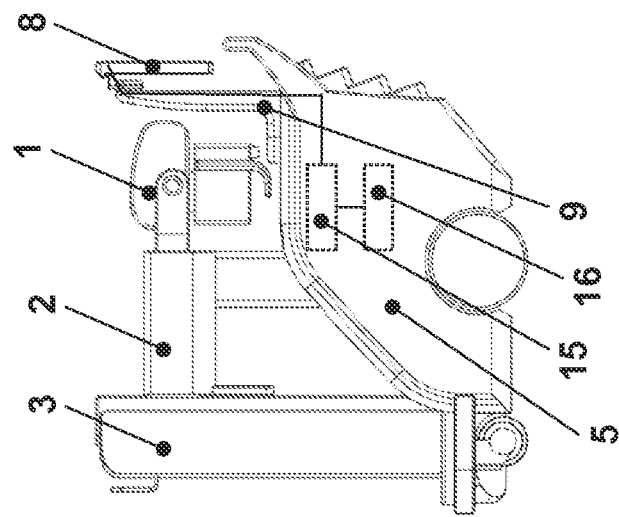

The movement of the monitor of the movable X-ray imaging apparatus according to the first embodiment will be described with reference to FIGS. 2A to 2C. FIG. 2A shows the position of the monitor 8 when the movable X-ray imaging apparatus has minimum outer dimensions. FIG. 2B shows a state in which the monitor 8 has tilted. FIG. 2C shows a state in which the monitor 8 has swiveled in the state shown in FIG. 2B. In the first embodiment, the tilt angle of the monitor 8 desirably falls within a movable range of 180° in the upward direction from the position of the monitor 8 shown in FIG. 2A. The swivel angle of the monitor 8 is desirably 90° in the left and right directions from the monitor position shown in FIG. 2A. This can realize an apparatus with good operability since the X-ray tube 1 does not interfere with the monitor 8 unless the arm 2 is extended in moving the X-ray tube 1 from its position in the moving form.

The swivel movement of the monitor 8 according to the first embodiment will be described in more detail with reference to FIGS. 3A and 3B. Reference numeral 17 denotes a rotation axis about which the monitor 8 swivels. FIG. 3A shows the position of the monitor 8 in the moving form shown in FIGS. 1A and 1B. FIG. 3B shows a state in which the monitor 8 has rotated about the swivel rotation axis 17 in the left direction by 90° by the swivel hinge 11. When the monitor 8 rotates in the left direction or the right direction (not shown), the rotation axis of the tilt hinge 10 becomes perpendicular to the moving surface of the cart unit 5. Pivoting the monitor 8 about the rotation axis perpendicular to the moving surface of the cart unit 5 enables the operator or doctor to check the display contents of the monitor 8 from various positions.

As described above, the monitor 8 is mounted on the cart unit 5 to be pivotable about two rotation axes, first and second rotation axes. More specifically, the monitor 8 is connected to a first member (the tilt hinge 10 and the monitor support member 12) which supports the monitor 8 to be pivotable about the first rotation axis. The first member is connected to a second member (the swivel hinge 11 and the monitor support arm 9) which supports the first member to be pivotable about the second rotation axis different from the first rotation axis. In this way, the monitor 8 is supported by the cart unit 5 to be pivotable about the first and second rotation axes. In the state (in which the rotation axis of the tilt hinge 10 is perpendicular to the moving surface) shown in FIG. 2C, the monitor 8 is provided with a rotation axis which is parallel to the display surface of the monitor 8 and perpendicular to the moving surface of the cart unit 5. As a result, it is possible to make the display surface of the monitor 8 turn from the right side to the back side of the movable X-ray imaging apparatus or from the left side to the back side of the movable X-ray imaging apparatus, thereby allowing the operator or doctor to readily check contents on the monitor 8.

The movable X-ray imaging apparatus according to the first embodiment includes a detection unit (not shown) for detecting the rotation state of the monitor 8 about the swivel rotation axis 17, and is configured to switch the display contents of the monitor 8 according to the detection result of the detection unit. As described above, the swivel rotation axis 17 is perpendicular to the display surface of the monitor 8. In this embodiment, therefore, as the rotation state of the monitor 8, a horizontally elongated state (landscape) and a vertically elongated state (portrait) can be provided. When the detection unit detects the horizontally elongated state (FIG. 3A) or the vertically elongated state (FIG. 3B) as the rotation state of the monitor 8, the display mode of the monitor 8 is switched according to the detection result, as will be described below. Note that examples of the arrangement of the detection unit for detecting the rotation state are:

- an arrangement for detecting the rotation angle about the swivel rotation axis 17 using a rotary encoder, and detecting whether the monitor 8 is in the horizontally elongated state or the vertically elongated state;
- an arrangement for detecting, using an acceleration sensor, whether the monitor 8 is in the horizontally elongated state or the vertically elongated state (with respect to gravity); and
- an arrangement for detecting the state of the monitor 8 using a mechanical switch which is turned on when the monitor 8 is in the horizontally elongated state and/or a mechanical switch which is turned on when the monitor 8 is in the vertically elongated state.

The display mode of the monitor 8 will be explained below with reference to FIGS. 4A to 6B. The monitor 8 according to the first embodiment displays a captured image used for checking by an operator or a captured image used for diagnosis by a doctor in addition to patient information indicating an imaging target patient, the location of the patient, and an examination information list. The user can perform various operations through the screen of the monitor 8. For example, it is possible to perform a login operation for giving the user an operation right, a logout operation for taking the operation right away from the user, an operation of activating/shutting down the whole or part of the apparatus, an operation of setting imaging conditions and transmitting a captured X-ray image to an intra-hospital network, and the like.

Figure 4B:
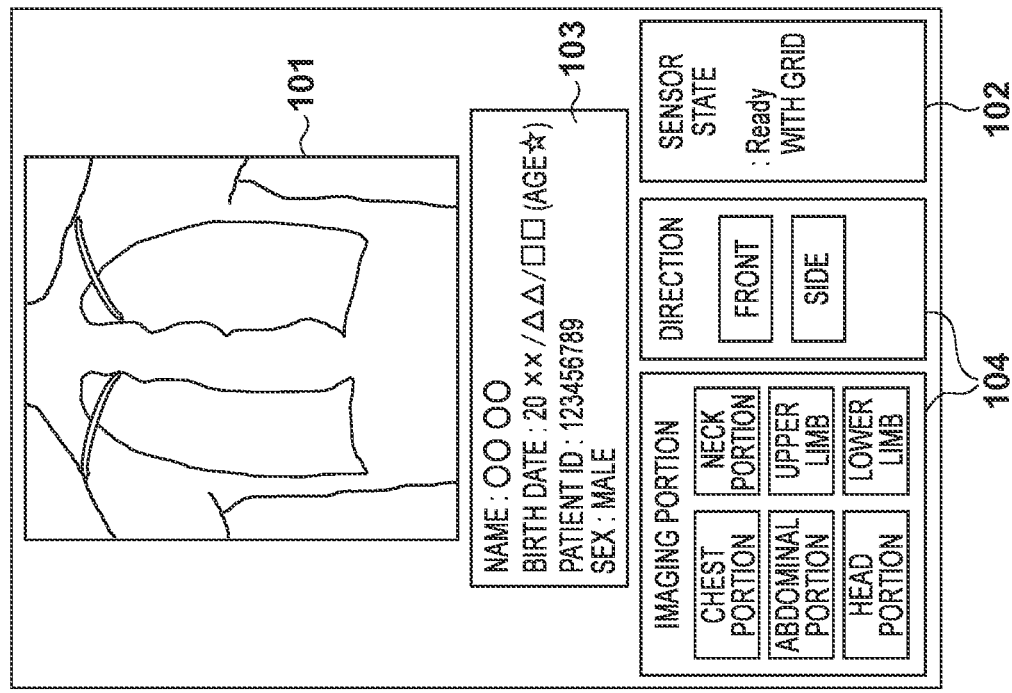
FIG. 4B is a view for explaining a display state in a portrait display mode.
Figure 4A:
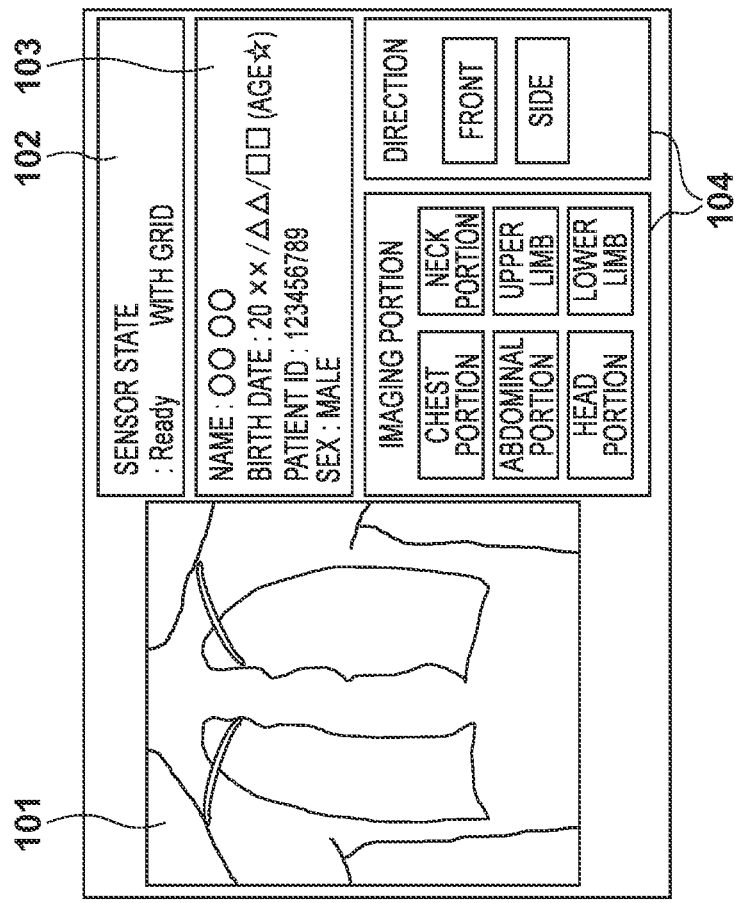
FIG. 4A is a view for explaining a display state in a landscape display mode.

FIG. 4A is a view for explaining a first display mode of the monitor 8 in which horizontally elongated (landscape) display is performed. FIG. 4B is a view for explaining a second display mode of the monitor 8 in which vertically elongated (portrait) display is performed. FIG. 4A shows a landscape display (first display mode) in the horizontally elongated state in which the shorter sides of the rectangular display area of the monitor 8 are set in the vertical direction. FIG. 4B shows a portrait display (second display mode) in the vertically elongated state in which the longer sides of the rectangular display area of the monitor 8 are set in the vertical direction.

An image display area 101 displays an X-ray image obtained by X-ray irradiation from the X-ray tube 1. A sensor state display area 102 displays the state of an X-ray image sensor. For example, the sensor state display area 102 displays an indication indicating that the sensor is preparing for imaging, the sensor is waiting for irradiation, the sensor is reading out image data, or the sensor is disabled, and displays an imaging disable state, a power source state, a communication state, and the presence/absence and type of a grid. A patient information display area 103 displays patient information such as the name and the birth date of an X-ray imaging target patient. Note that the patient information display area 103 may display the location information (hospital room) of a patient. A condition setting area 104 provides a user interface for setting X-ray imaging conditions (for example, a tube voltage, tube current, and exposure time). The monitor 8 according to this embodiment includes a touch panel. Each of FIGS. 4A and 4B shows a state in which the user can set imaging conditions such as an imaging portion and imaging direction in the condition setting area 104.

The display contents shown in FIGS. 4A and 4B are merely an example, and other information about X-ray imaging may be displayed. As described above, in the display mode switching processing shown in FIGS. 4A and 4B, the display contents remain the same but the layouts of the pieces of information are different between the horizontally elongated display and the vertically elongated display. According to the result of detecting the rotation state of the monitor 8 about the swivel rotation axis 17 by the detection unit described above, the monitor display is switched to the landscape display (FIG. 4A) or the portrait display (FIG. 4B). The operator or doctor can select a monitor display suitable for the attitude of the monitor 8, thereby improving the operability.

Another example of the processing of switching the display mode according to detection of the rotation state of the monitor 8 by the detection unit will be described with reference to FIGS. 5A and 5B. In the first display mode shown in FIG. 5A, display contents are the same as those shown in FIG. 4A but the image display area 101 displays an image which is acceptable to an X-ray imaging operator to determine whether to perform imaging again. For example, an image obtained by executing low-resolution processing for an X-ray image.

Figure 5B:
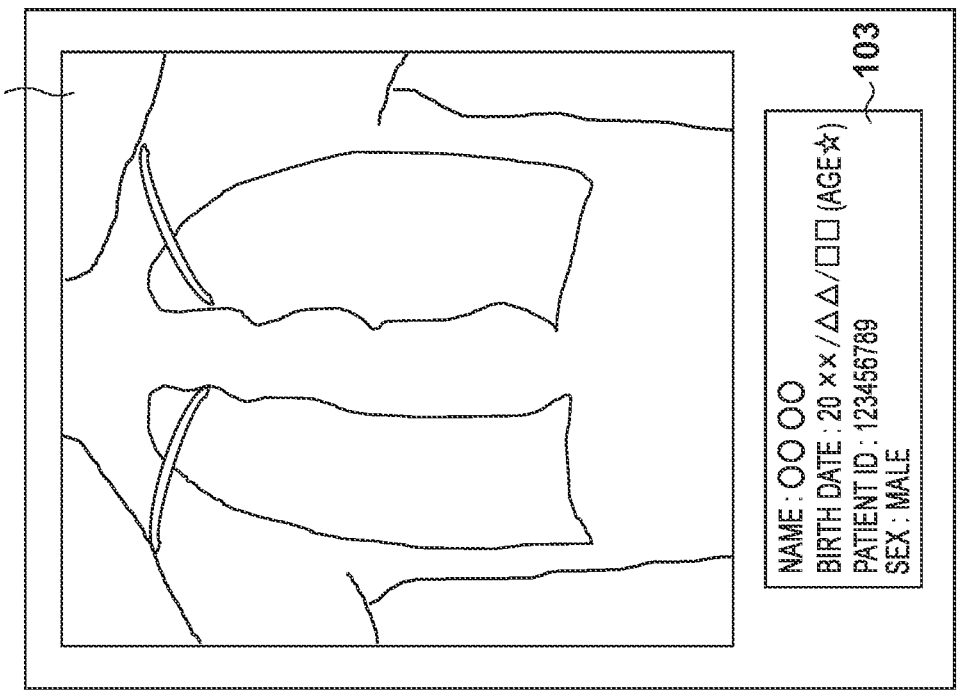
FIGS. 5A and 5B are views for explaining display states in an image processing mode and non-image processing mode.
Figure 5A:
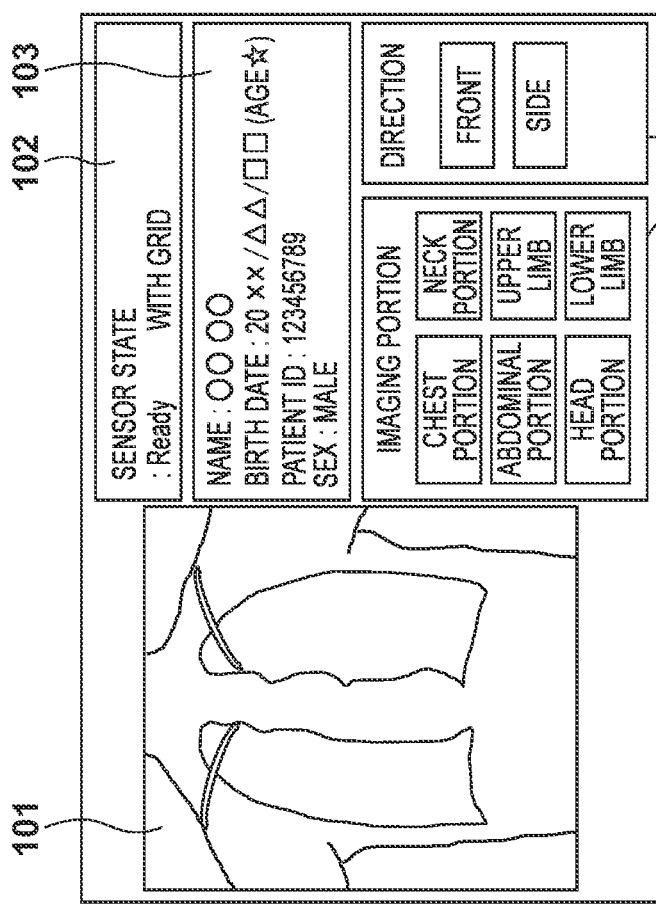

On the other hand, in the second display mode shown in FIG. 5B, a layout corresponding to the vertically elongated display is adopted and the image display area 101 displays an X-ray image with which the doctor can perform image diagnosis. That is, an image display area 101a shown in FIG. 5B displays an X-ray image having a resolution higher than that of the image displayed in the image display area 101 shown in FIG. 5A. Therefore, the image display area 101a displays an image obtained by executing high-resolution processing and/or image processing for suppressing grid stripes on the X-ray image. Note that image processing may be arbitrarily selected. Furthermore, as shown in FIG. 5B, information such as the patient information display area 103 other than a diagnostic image may be added. Note that since the second display mode shown in FIG. 5B has as its object to present a diagnostic image, a user interface for, for example, setting an imaging portion is not displayed. In the above-described display mode switching processing, it is possible to provide a monitor display suitable for observation by selectively performing image processing for displaying a diagnostic image, which requires a processing time, thereby improving the operability.

Still another example of the display mode switching processing will be explained with reference to FIGS. 6A and 6B. A case in which an X-ray imaging setting display mode is used as the first display mode of the monitor 8 and a diagnostic image display mode is used as the second display mode of the monitor 8 will be described with reference to FIGS. 6A and 6B. FIG. 6A shows the X-ray imaging setting display mode in which the user can log into the movable X-ray imaging apparatus by operating a login button 106, and perform various operations for the apparatus upon login. A shutdown button 107 is used to turn off the power of the apparatus when it is erroneously activated. An "other" button 108 is a button for making other settings, and is used to select items which are not displayed. In other settings, it is also possible to freely increase/decrease the number of selection buttons.

An examination information acquisition button 109 is a button for acquiring an examination information list. When this button is operated, the apparatus communicates with the intra-hospital network to acquire examination information. A patient position button 110 is a button for viewing patient position information. When the patient position button 110 is selected, a hospital map and hospital room information of an examination target patient are displayed in the image display area 101. An image transmission button 111 is a button for transmitting an image to the intra-hospital network, and is used to transmit an image captured before selection.

An examination information selection button 112 is a button for selecting examination information, and is used to select an imaging portion and an imaging body posture based on the examination information list acquired by operating the examination information acquisition button 109. A patient information button 113 is a button for displaying patient information. As described above, the patient information includes the name, age, patient ID, and sex of a patient, and the user can confirm the patient with the information. An imaging condition setting button 114 is a button for making imaging condition settings, and can be used to set a tube current, a tube voltage, an X-ray irradiation time, and the like.

Figure 6B:
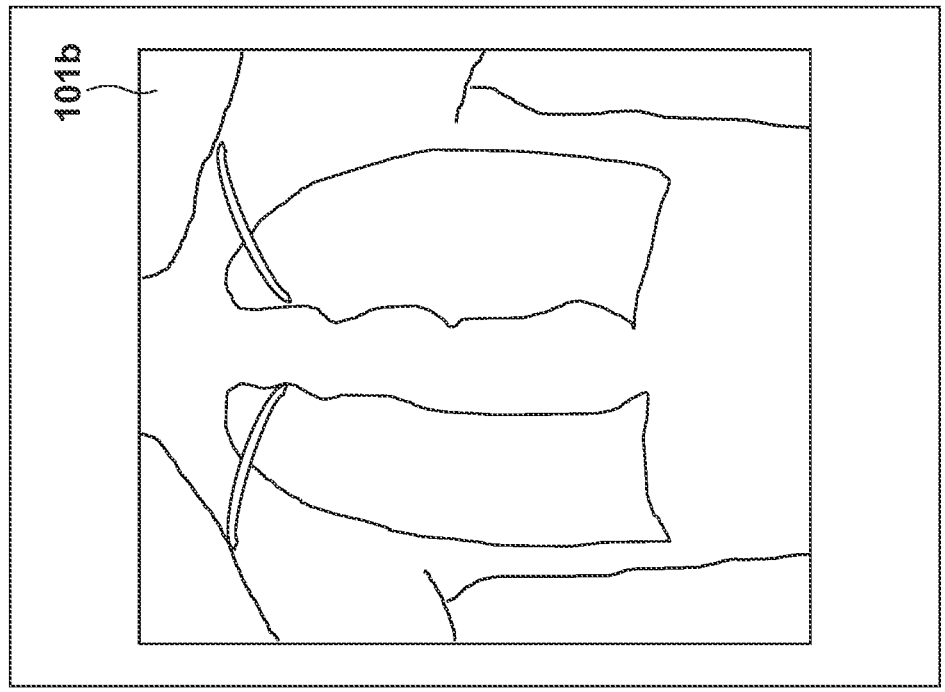
FIGS. 6A and 6B are views for explaining an X-ray imaging setting mode and a diagnostic image display mode.
Figure 6A:
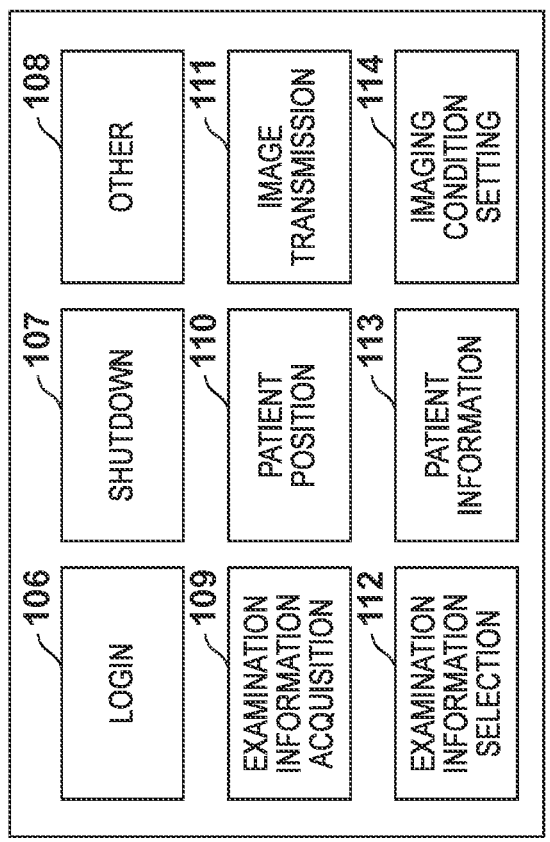

FIG. 6B shows an example of a display in the diagnostic image display mode, in which an image display area 101b for displaying a diagnostic image is displayed. Note that some of the set imaging conditions may be displayed in an area other than the image display area 101b within the display enable area of the monitor 8. This makes it possible to select X-ray imaging settings or image diagnostic in accordance with the rotation state of the monitor 8 and allows a monitor display according to the current situation in an operating room, thereby improving the operability.

Note that in the display mode content switching processing shown in FIGS. 5A and 5B or 6A and 6B, the screen for making imaging settings is presented in the horizontally elongated state and the screen for displaying a diagnostic image is presented in the vertically elongated state. However, this may be reversed. That is, the screen for making imaging settings may be presented in the vertically elongated state and the screen for displaying a diagnostic image may be presented in the horizontally elongated state. Furthermore, the display contents and the combination of the state and screen in the first display mode or the second display mode are not limited to the above example.

A control arrangement for switching the monitor contents described above with reference to FIGS. 4A to 6B will be explained with reference to FIGS. 2A to 2C. In FIGS. 2A to 2C, a monitor display control unit 15 switches the display mode (display contents) of the monitor 8 according to its rotation state detected by the detection unit (not shown). An imaging control unit 16 controls setting of X-ray imaging conditions and execution of X-ray imaging via the monitor 8 (touch panel). Note that although each control unit and the monitor 8 communicate with each other by wired connection in FIGS. 2A to 2C, wireless communication may be used. Communication connection between the detection unit and the monitor display control unit 15 or imaging control unit 16 may be wired or wireless connection.

Figure 7:
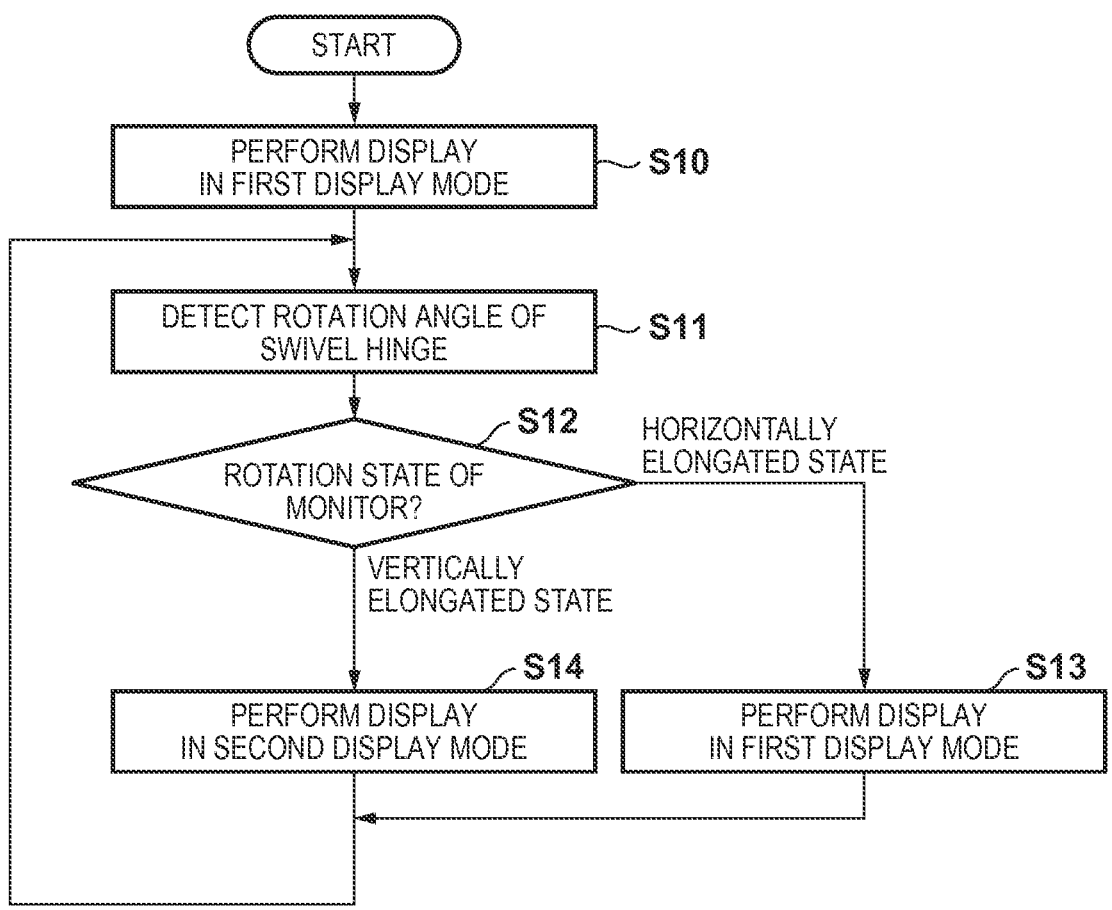
FIG. 7 is a flowchart illustrating monitor display mode switching processing according to the first embodiment.

FIG. 7 is a flowchart for explaining processing of a system according to the first embodiment. In step S10, upon activation of the apparatus or start of imaging, the monitor display control unit 15 performs display in the first display mode. In this embodiment, display in the first display mode in which display contents when the rotation state of the monitor 8 is the horizontally elongated (landscape) state are displayed is executed. The present invention, however, is not limited to this. For example, upon activation of the apparatus, display in the second display mode in which display contents when the rotation state of the monitor 8 is the vertically elongated (portrait) state are displayed may be executed. Alternatively, display may be started after detection of the rotation state by the detection unit (that is, step S10 may be omitted).

In step S11, the monitor display control unit 15 acquires the result of detection of the rotation state of the monitor 8 by the detection unit. In the arrangement shown in FIGS. 1A to 3B, the monitor display control unit 15 acquires the rotation angle of the swivel hinge 11, and detects the rotation state of the monitor 8 (step S12). If the detected rotation state is the horizontally elongated (landscape) state, the process advances from step S12 to step S13, and the monitor display control unit 15 performs display on the monitor 8 in the first display mode. On the other hand, if it is detected that the rotation state is the vertically elongated (portrait) state, the process advances from step S12 to step S14, and the monitor display control unit 15 performs display on the monitor 8 in the second display mode.

Note that it may be detected that the monitor 8 is in an intermediate state which is neither the vertically elongated state nor the horizontally elongated state. If such intermediate state is detected, the process may return from step S12 to step S11, and the display mode at this time may be maintained. Consider, for example, a case in which the detection unit is configured to output a signal indicating the horizontally elongated state when the rotation angle of the swivel hinge 11 falls within the range from 0 to 15°, to output a signal indicating the vertically elongated state when the rotation angle falls within the range from 75 to 90°, and to output no signal when the rotation angle falls within the range from 15 to 75°. In this case, when the rotation angle falls within the range from 15 to 75°, the monitor 8 is in an intermediate state (a state in which no signal is output) which is neither the vertically elongated state nor the horizontally elongated state. Alternatively, an intermediate state exists when the detection unit is formed by a switch which is turned on when the rotation angle is 0° or close to it and a switch which is turned on when the rotation angle is 90° or close to it.

In step S13, if the display mode until now is the second display mode, the display contents are switched to those in the first display mode. However, if the display mode until now is the first display mode, the display contents are not changed. In this case, the processing is equivalent to skipping step S13. Similarly, in step S14, if the display mode until now is the first display mode, the display contents are switched to those in the second display mode. However, if the display mode until now is the second display mode, the display contents are not changed. In this case, the processing is equivalent to skipping step S14.

With the above-described processing, the display mode of the monitor 8 is switched according to detection of rotation of the monitor 8 about the swivel rotation axis 17, and the display contents of the monitor are changed as shown in FIGS. 4A to 6B. Assume that the user manually moves (swivels or tilts and rotates) the monitor 8. However, a driving mechanism using a motor or the like may move the monitor 8. In the aforementioned embodiment, the display mode is switched according to the rotation position (rotation angle) of the swivel hinge 11. The present invention, however, is not limited to this. For example, a switch for explicitly instructing to switch the display mode may be provided.

With the above-described arrangement, it is possible to select the display contents of the monitor 8 according to the attitude of the monitor 8, and the doctor can perform image diagnosis using the monitor 8, thereby providing a movable X-ray imaging apparatus with improved operability. That is, the operator or doctor can see appropriate monitor information according to the attitude of the monitor 8. This allows setting of X-ray imaging and X-ray image diagnosis using one monitor 8 on a movable X-ray imaging machine even in an operating room, thereby performing an efficient operation.

As described above, the movable X-ray imaging apparatus according to the first embodiment enables the doctor or operator to readily check the contents of the monitor. It is possible to set X-ray imaging and perform X-ray image diagnosis, thereby improving the operability of the operator or doctor.

Note that in the aforementioned embodiment, the two display modes are switched depending on whether the rotation state of the monitor 8 is the horizontally elongated state or the vertically elongated state. By adding the rotation state of the second rotation axis, more than two display modes may be switched.

[Second Embodiment]

In the first embodiment, the arrangement in which the tilt hinge 10 provides a rotation axis along one side of the monitor 8 as the first rotation axis, and the swivel hinge 11 provides a rotation axis perpendicular to the screen of the monitor 8 as the second rotation axis has been explained. However, the combination of the first rotation axis and the second rotation axis is not limited to this. In the second embodiment, as another example of the combination of rotation axes for a monitor 8, an arrangement in which a rotation axis along one side of the monitor 8 is used as a first rotation axis and a rotation axis perpendicular to the moving surface of a cart unit 5 is used as a second rotation axis will be described.

Figure 8A:
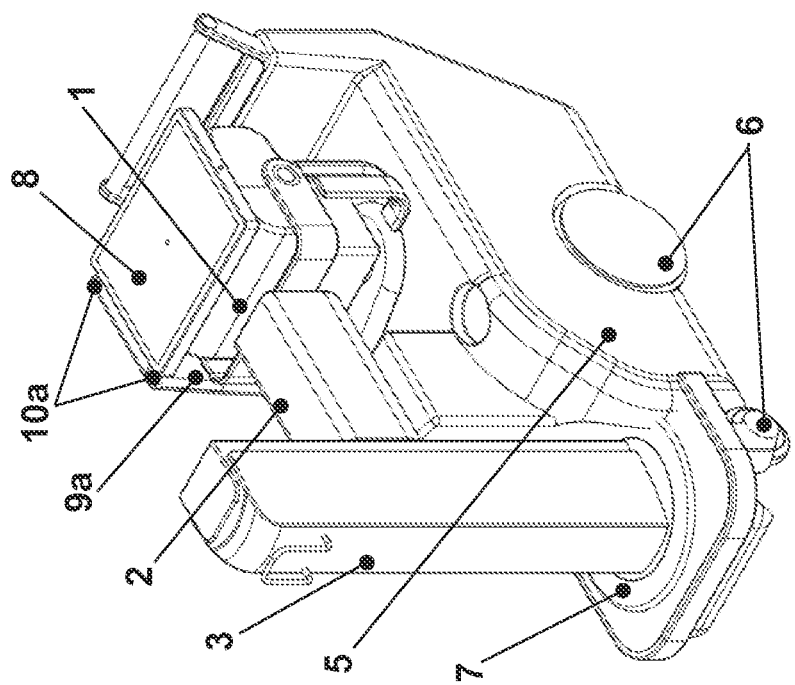
FIGS. 8A and 8B are views each showing the outer appearance of a movable X-ray imaging apparatus according to the second embodiment.
Figure 8B:
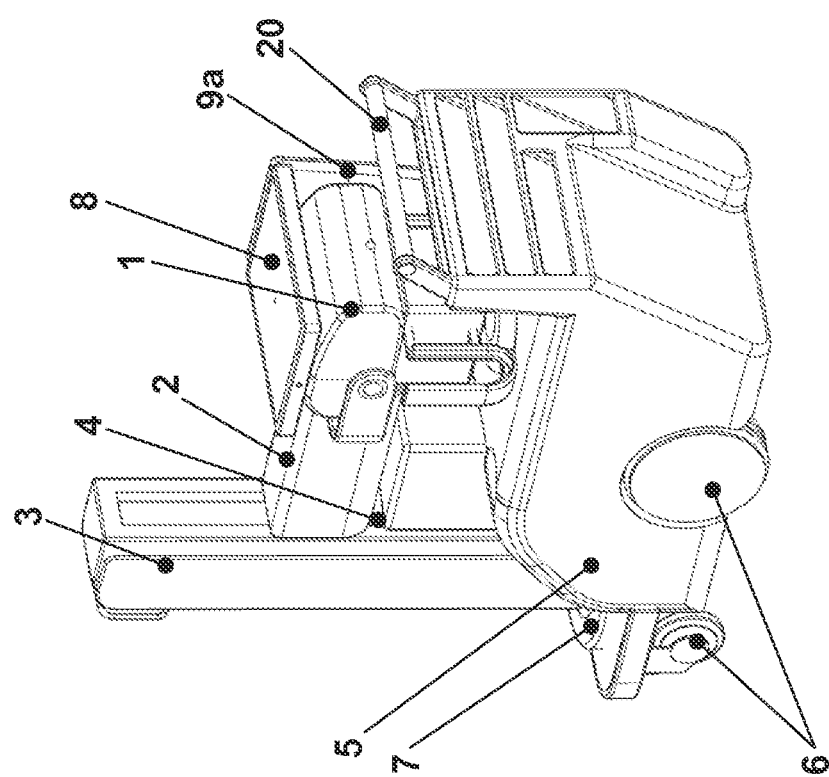

FIGS. 8A and 8B are views each showing the arrangement of a movable X-ray imaging apparatus according to the second embodiment of the present invention. FIG. 8A is a perspective view showing the moving form of the apparatus when seen from the back side. FIG. 8B is a perspective view showing the moving form of the apparatus when seen from the front side. In the second embodiment, in the moving form, the monitor 8 is located above an X-ray tube 1.

Referring to FIGS. 8A and 8B, the same components as those in the first embodiment (FIGS. 1A and 1B) have the same reference numerals. The monitor 8 is supported by a monitor support arm 9a arranged on the upper portion of the cart unit 5. Tilt hinges 10a are attached to the monitor support arm 9a so that the monitor 8 tilts, and provides the first rotation axis. The tilt hinges 10a are desirably torque hinges which can flexibly hold the attitude of the monitor 8 but may be a combination of damper hinges or torque hinges each having low torque and including a mechanism which can lock at an arbitrary hinge opening angle. Alternatively, a mechanism which can lock the position of the monitor 8 at only a desirable monitor angle may be provided.

FIGS. 9A and 9B are views for explaining the movement of the monitor according to the second embodiment. A rotation axis 14 is the rotation axis of a turning unit which supports the monitor support arm 9a on the cart unit 5 to be turnable, and corresponds to the second rotation axis. The turning unit can make the monitor support arm 9a turn about the rotation axis 14, thereby causing the monitor 8 to turn. To do this, the monitor support arm 9a and the cart unit 5 are desirably connected to each other by, for example, a swivel hinge. FIG. 9A shows a state in which the monitor 8 has tilted from the state shown in FIG. 8A to stand upright. FIG. 9B shows a state in which the X-ray tube 1 has moved from the state shown in FIG. 9A and the monitor 8 has rotated about the rotation axis 14. In the second embodiment, the tilt angle of the monitor desirably falls within a movable range of 90° in the upward direction from the monitor position shown in FIG. 9A.

For switching the display mode (display contents) of the monitor 8, a function similar to that described in the first embodiment can be provided. Note that in the second embodiment, instead of switching the display mode depending on whether the rotation state of the monitor 8 is the horizontally elongated state or the vertically elongated state, the display mode is switched according to the rotation position of one of the first and second rotation axes or the combination of the rotation positions of the first and second rotation axes. That is, the display mode of the monitor 8 is switched according to the turning angle of the turning unit which makes the monitor 8 turn. Furthermore, an arrangement which can pivot the monitor 8 about a rotation axis perpendicular to the display surface of the monitor 8 may be added to switch the display mode depending on whether the monitor 8 is in the horizontally elongated state or the vertically elongated state, similarly to the first embodiment.

With the above-described arrangement, according to the second embodiment, the display surface of the monitor 8 can continuously pivot from the right side to the left side through the back side of the movable X-ray imaging apparatus, thereby allowing an operator or doctor to readily check the contents of the monitor 8. Furthermore, as compared with the first embodiment, the movable range of the monitor 8 can be made wider, and the monitor can be made closer to the doctor especially when used in an operating room, thereby providing a movable X-ray imaging apparatus which allows more efficient image diagnosis.

[Third Embodiment]

The arrangement of a movable X-ray imaging apparatus according to the third embodiment of the present invention will be described with reference to FIGS. 10A to 10C. In the second embodiment, the arrangement in which the monitor 8 is located above the X-ray tube 1 in the moving form has been explained. In the third embodiment, however, a monitor 8 is located below an X-ray tube 1 in a moving form.

Each of FIGS. 10A to 10C is a side view showing the apparatus. FIG. 10A shows the moving form of the apparatus. FIG. 10B shows a state in which the X-ray tube 1 has risen from the state of the moving form shown in FIG. 10A and the monitor 8 has tilted to stand upright. FIG. 10C shows a state in which the monitor 8 has turned about a rotation axis 14.

Referring to FIGS. 10A to 10C, the same components as those in the first embodiment (FIGS. 1A and 1B) have the same reference numerals. Instead of the L-shaped member described in the second embodiment (FIGS. 9A and 9B), a monitor support arm 9b is a plate-like member (or an L-shaped member including a short upright portion), at the end portion of which the monitor 8 is arranged via a tilt hinge 10b. As described in the first and second embodiments, an arrangement for switching the display mode of the monitor 8 can also be provided. More specifically, the display mode of the monitor 8 is switched according to the upright state of the monitor 8 and the turning angle of a turning unit. The upright state indicates whether the monitor 8 stands upright or not. Alternatively, an arrangement which can pivot the monitor 8 about a rotation axis perpendicular to the display surface of the monitor 8 may be added to switch the display mode depending on whether the monitor 8 is in the horizontally elongated state or the vertically elongated state, similarly to the first embodiment.

The arrangement according to the third embodiment also considers the interference between the X-ray tube 1 and the monitor 8. FIG. 11A shows the state of the apparatus at the time of X-ray exposure. FIG. 11B shows a state in which the monitor 8 is accommodated when the X-ray tube 1 is accommodated. A column rotating unit 7 includes a rotation angle sensor 18 of a column 3 with respect to a cart unit 5. The tilt hinge 10b includes a motor (not shown), and changes the angle of the monitor 8 under the control of a monitor angle control unit 19. Note that each control unit, the rotation angle sensor 18, and the motor of the tilt hinge 10b communicate with each other by wired connection in FIGS. 11A and 11B but may communicate with each other using wireless communication.

Figure 12:
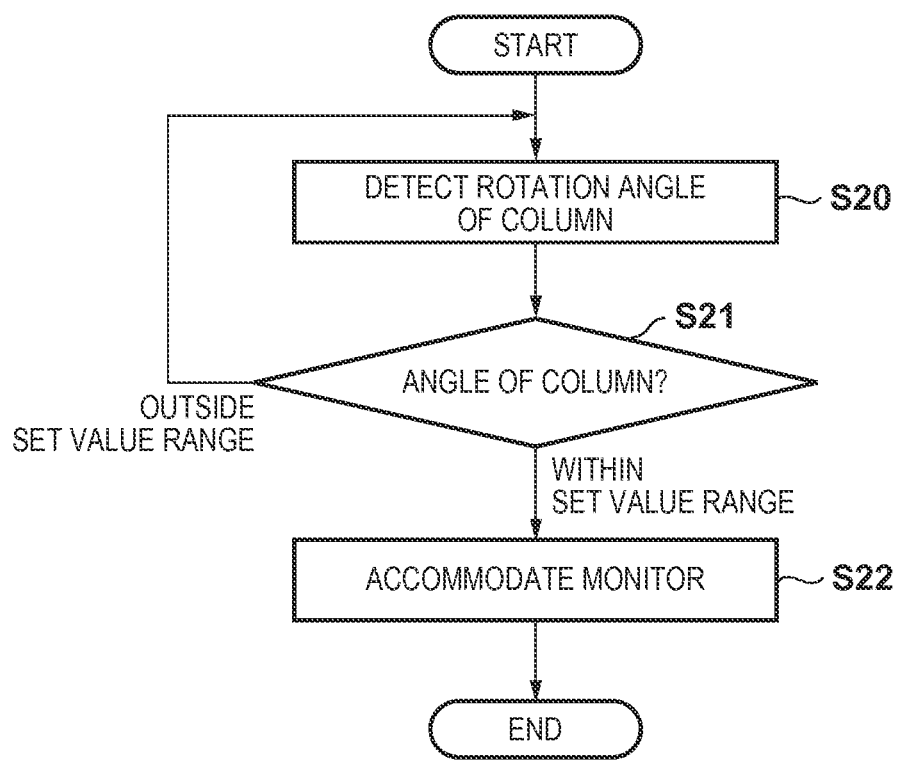
FIG. 12 is a flowchart illustrating the monitor accommodation system according to the third embodiment.

FIG. 12 is a flowchart illustrating a system according to the third embodiment. When the user rotates the column 3 upon start of X-ray imaging, in step S20 the rotation angle sensor 18 detects the rotation angle of the column 3. In step S21, an imaging control unit 16 determines whether the rotation angle of the column 3 falls within a preset angle range. If the rotation angle of the column 3 falls within the preset range, the process advances to step S22; otherwise, the process returns to step S20. In step S22, the monitor angle control unit 19 receives a driving signal from the imaging control unit 16, and drives the motor of the tilt hinge 10b to move the monitor 8 to the position of the moving form shown in FIG. 10A. With the above-described processing, for example, when an operator rotates the column 3 supporting the X-ray tube 1 to the state shown in FIG. 11B upon end of imaging, the monitor 8 automatically moves from the upright state to a state (monitor accommodation state) almost parallel to the moving surface of the cart unit 5. The operator, therefore, can smoothly set the movable X-ray imaging apparatus in the moving form.

With the above-described arrangement, as compared with the second embodiment, it is possible to accommodate the X-ray tube 1 at the accommodation position in the moving form irrespective of the rotation position of the monitor 8 about the rotation axis 14, thereby providing a movable X-ray imaging apparatus with improved operator's operability.

[Fourth Embodiment]

In the first to third embodiments, the first rotation axis along one side of the monitor 8 and the second rotation axis different from the first rotation axis are orthogonal to each other. The present invention is not limited to this. In the fourth embodiment, an arrangement in which a first rotation axis and a second rotation axis are parallel to each other will be explained. Note that in the fourth embodiment, an arrangement in which the second rotation axis coincides with the rotation axis of a column 3, that is, an arrangement in which an arm supporting a monitor 8 is part of the column 3 is provided.

Figure 13A:
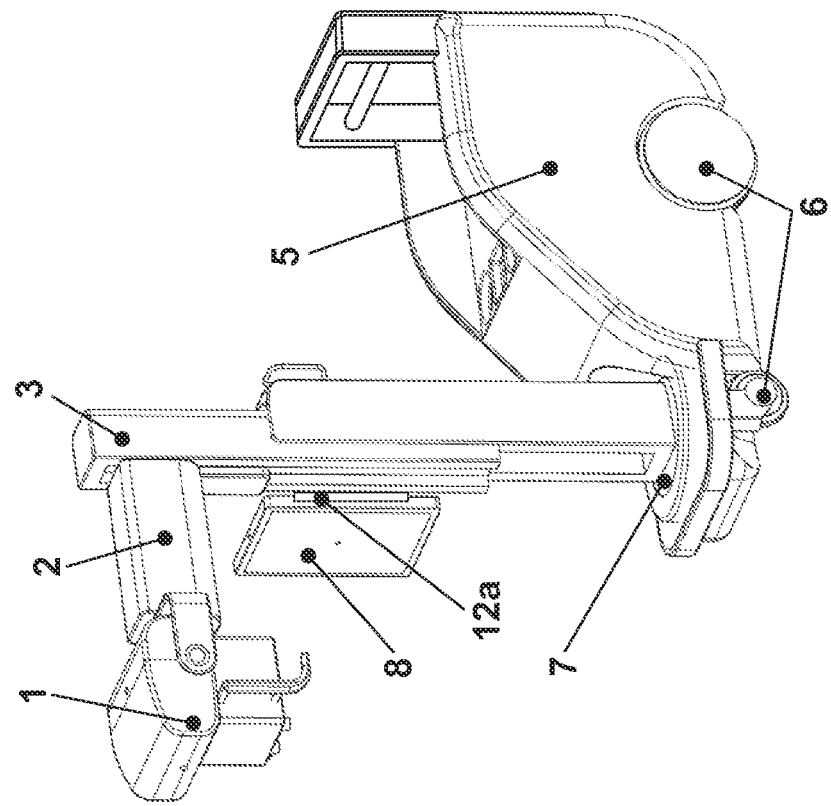
FIGS. 13A and 13B are views each showing the outer appearance of a movable X-ray imaging apparatus according to the fourth embodiment.
Figure 13B:
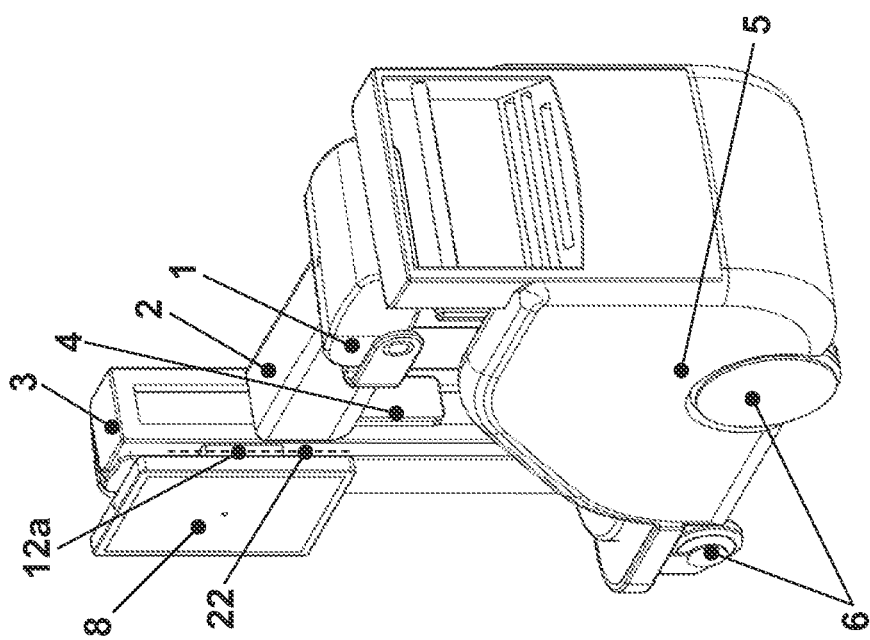

FIGS. 13A and 13B are views each showing the arrangement of a movable X-ray imaging apparatus according to the fourth embodiment. In FIGS. 13A and 13B, the same components as those in the first embodiment (FIGS. 1A and 1B) have the same reference numerals. FIG. 13A is a perspective view showing the moving form of the apparatus when seen from the back side. FIG. 13B is a perspective view showing the apparatus at the time of imaging when seen from the front side. In the movable X-ray imaging apparatus according to the fourth embodiment, the column 3 holding an X-ray tube 1 and a monitor support member 12a supporting the monitor 8 are connected via a tilt hinge.

The display contents of the monitor 8 are as described in the first embodiment. The monitor 8 is supported by the monitor support member 12a arranged on a side surface of the column 3. The monitor support member 12a includes a tilt hinge for tilting the monitor 8. The tilt hinge of the monitor support member 12a is attached so that the monitor 8 rotates about the monitor support member 12a. The direction of the tilt rotation axis is along one side of the display surface of the monitor 8 and parallel to the column 3. The tilt hinge of the monitor support member 12a is desirably a torque hinge which can flexibly hold the attitude of the monitor 8 but may be a combination of damper hinges or torque hinges each having low torque and including a mechanism which can lock at an arbitrary hinge opening angle. Alternatively, a mechanism which can lock the monitor position at only a desirable monitor angle may be provided.

In the fourth embodiment, the display mode of the monitor 8 may be switched, similarly to the second embodiment. Furthermore, in order to switch the display of the monitor 8 between a landscape display and a portrait display, the monitor support member 12a and the monitor 8 may be connected to each other by a swivel hinge 11 as described in the first embodiment. Such arrangement allows switching of the display contents of the monitor 8 (switching between the landscape state and the portrait state), as described in the first embodiment. Furthermore, the monitor 8 may be configured to be attached/detached to/from the monitor support member 12a by a one-step operation.

With the above-described arrangement, it is possible to make the monitor 8 closer to a doctor, as compared with the first embodiment, thereby providing a movable X-ray imaging apparatus which allows more efficient image diagnosis especially when used in an operating room.

The monitor 8 may include a battery and memory to store images displayed so far and to retrieve and display the image. By configuring the monitor 8 to be detachable, an operator can carry the monitor 8 near a doctor who is operating, and make the monitor 8 close to the doctor. Furthermore, for example, when used for an emergency visit, a doctor can explain the condition of a patient to his/her family who is waiting outside an emergency room by using the monitor 8.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-028345, filed Feb. 15, 2013, which is hereby incorporated by reference herein in its entirety.

What is claimed is:

1. A movable X-ray generation apparatus comprising:
an X-ray tube configured to perform irradiation with X-rays;
an arm configured to support the X-ray tube, the arm including an extending mechanism for extending the arm to move the X-ray tube in a horizontal direction;
a column configured to support the arm;
a cart unit configured to support the column and move the arm,
wherein the X-ray tube is configured to be moved into and out of an accommodation configuration;
a monitor, including a screen;
a monitor support arm, mounted on an upper portion of the cart unit, configured to support the monitor, wherein the monitor support arm is located at a position where the X-ray tube does not interfere with the monitor in a state in which the X-ray tube is in the accommodation configuration, unless the arm is extended by the extending mechanism;
a first member configured to support the monitor to be pivotable about a first rotation axis; and
a second member configured to support the first member to be pivotable about a second rotation axis different from the first rotation axis,
wherein at least one of the first rotation axis and the second rotation axis is perpendicular to a moving surface on which the cart unit moves, and
wherein the X-ray tube is between the column and the monitor when in the accommodation state.

2. The apparatus according to claim 1, wherein the first rotation axis is a rotation axis along one side of said monitor, and the second rotation axis is a rotation axis perpendicular to the moving surface.

3. The apparatus according to claim 2, wherein the second member is arranged such that the first rotation axis becomes perpendicular to the moving surface by pivoting of said second member about the second rotation axis.

4. The apparatus according to claim 3, wherein the first member is arranged such that the second rotation axis is movable to be parallel to the screen of the monitor and perpendicular to the moving surface by pivoting the monitor about the first rotation axis so that the screen of the monitor stands upright with respect to the moving surface.

5. The apparatus according to claim 1, further comprising a switching unit configured to switch the monitor between a first display mode and a second display mode.

6. The apparatus according to claim 5, wherein the switching unit is configured to switch display modes based on at least one of a rotation position of said monitor about the first rotation axis and a rotation position of the monitor about the second rotation axis.

7. The apparatus according to claim 5, further comprising a switching unit configured to perform display on the monitor in the first display mode when said monitor pivots about the second rotation axis and enters a landscape state, and perform display on the monitor in the second display mode when the monitor enters a portrait state.

8. The apparatus according to claim 7, wherein display is performed on the monitor in a layout corresponding to the landscape state in the first display mode, and display is performed on the monitor in a layout corresponding to the portrait state in the second display mode.

9. The apparatus according to claim 5, wherein a screen for imaging setting is displayed on the monitor in the first display mode, and a screen for displaying a captured diagnostic image is displayed on the monitor in the second display mode.

10. The apparatus according to claim 1, wherein the first and second members are arranged such that the first and second rotation axes are offset from each other.

11. The apparatus according to claim 1, wherein, when the X-ray tube is in the accommodation state, the screen of the monitor faces away from the X-ray tube.

* * * * *